United States Patent
Deur-Bert et al.

(10) Patent No.: US 9,458,071 B2
(45) Date of Patent: *Oct. 4, 2016

(54) METHOD FOR SEPARATING AND RECOVERING 2,3,3,3-TETRAFLUOROPROPENE AND HYDROFLUORIC ACID

(71) Applicant: Arkema France, Colombes (FR)

(72) Inventors: Dominique Deur-Bert, Charly (FR); Bertrand Collier, Saint-genis-laval (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,493

(22) Filed: Jan. 14, 2016

(65) Prior Publication Data

US 2016/0130200 A1    May 12, 2016

Related U.S. Application Data

(63) Continuation of application No. 14/131,036, filed as application No. PCT/FR2012/051327 on Jun. 14, 2012, now Pat. No. 9,266,799.

(30) Foreign Application Priority Data

Jul. 8, 2011 (FR) .................... 11 56208

(51) Int. Cl.
| | |
|---|---|
| *C07C 17/25* | (2006.01) |
| *C07C 17/20* | (2006.01) |
| *C07C 17/38* | (2006.01) |
| *C07C 17/383* | (2006.01) |
| *C07C 17/42* | (2006.01) |
| *C01B 7/19* | (2006.01) |
| *C07C 17/35* | (2006.01) |

(52) U.S. Cl.
CPC ............... *C07C 17/42* (2013.01); *C01B 7/195* (2013.01); *C07C 17/20* (2013.01); *C07C 17/206* (2013.01); *C07C 17/25* (2013.01); *C07C 17/35* (2013.01); *C07C 17/38* (2013.01); *C07C 17/383* (2013.01)

(58) Field of Classification Search
CPC ..... C07C 17/20; C07C 17/25; C07C 17/206; C07C 17/38; C07C 17/383
See application file for complete search history.

(56) References Cited

U.S. PATENT DOCUMENTS

| | | | |
|---|---|---|---|
| 7,803,975 B2 | 9/2010 | Knapp | |
| 8,058,486 B2 | 11/2011 | Merkel et al. | |

FOREIGN PATENT DOCUMENTS

| | | |
|---|---|---|
| CN | 101597209 A | 12/2009 |
| WO | 2008/008519 A2 | 1/2008 |
| WO | 2008/040969 A2 | 4/2008 |
| WO | 2008/054781 A1 | 5/2008 |
| WO | 2009/105512 A1 | 8/2009 |
| WO | 2011/059078 A1 | 5/2011 |
| WO | 2012/098420 A1 | 7/2012 |

*Primary Examiner* — Medhanit Bahta
(74) *Attorney, Agent, or Firm* — Brinks Gilson & Lione

(57) ABSTRACT

The present invention relates to a method for separating a composition containing 2,3,3,3-tetrafluoropropene and hydrofluoric acid, and for recovering the thus-separated 2,3,3,3-tetrafluoropropene and hydrofluoric acid. The invention also relates to a method for manufacturing and purifying 2,3,3,3-tetrafluoropropene using a hydrofluorination reaction of the saturated or unsaturated compound having three carbon atoms and including at least one chlorine atom in the presence of a fluorination catalyst.

11 Claims, 1 Drawing Sheet

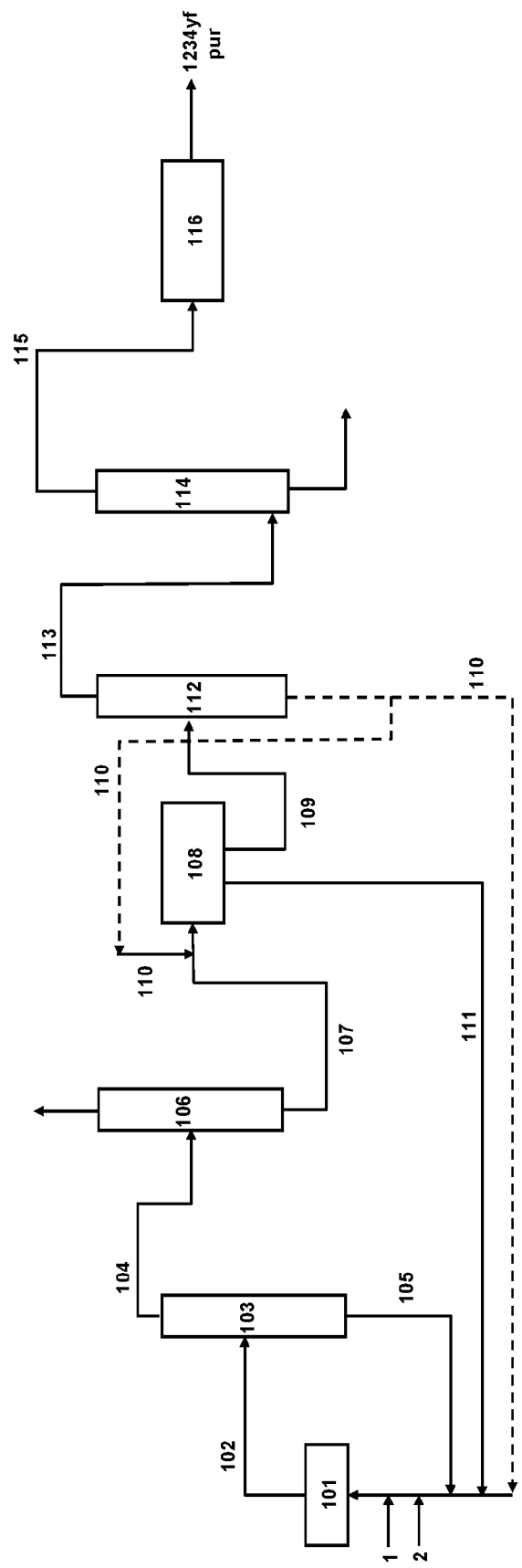

METHOD FOR SEPARATING AND RECOVERING 2,3,3,3-TETRAFLUOROPROPENE AND HYDROFLUORIC ACID

This application is a Continuation of U.S. patent application Ser. No. 14/131,036 filed Jun. 5, 2014, now allowed; which is a National Stage application of International Application No. PCT/FR2012/051327 filed Jun. 14, 2012; which claims the benefit of French Application No. 1156208, filed Jul. 8, 2011.

The present invention relates to a process for the separation of a composition including 2,3,3,3-tetrafluoropropene and hydrofluoric acid and for the recovery of the 2,3,3,3-tetrafluoropropene and hydrofluoric acid thus separated.

The choice of a heat-transfer fluid is dictated, on the one hand, by the thermodynamic properties of the fluid and, on the other hand, by additional constraints. Thus, a particularly important criterion is that of the impact of the fluid under consideration on the environment.

The problems presented by substances which deplete the atmospheric ozone layer were dealt with at Montreal, where the protocol was signal imposing a reduction in the production and use of chlorofluorocarbons (CFCs). This protocol has formed the subject of amendments which have required the abandoning of CFCs and have extended regulation to other products, including hydrochlorofluorocarbons (HCFCs).

The refrigeration and air conditioning industries have invested a great detail in the replacement of these refrigerants and it is because of this that hydrofluorocarbons (HFCs) have been marketed.

In the motor vehicle industry, the air conditioning systems of the vehicles sold in many countries have moved from a refrigerant comprising the chlorofluorocarbon (CFC-12) to that of the hydrofluorocarbon (1,1,1,2-tetrafluoroethane: HFC-134a), which is less harmful to the ozone layer. However, from the viewpoint of the objective set by the Kyoto protocol, HFC-134a (GWP=1430) is regarded as having a high heating power. The contribution to the greenhouse effect of a refrigerant is quantified by a criterion, the GWP (Global Warming Potential), which summarizes the heating power by taking a reference value of 1 for carbon dioxide.

2,3,3,3-Tetrafluoropropene (HFO-1234yf), as a result of its low GWP, is considered a potential candidate for the replacement of HFC-134 in motor vehicle air conditioning.

2,3,3,3-Tetrafluoropropene is generally prepared by reacting a chlorinated or fluorinated/chlorinated hydrocarbon compound in the presence of a greater than stoichiometric amount of hydrofluoric acid (WO 2008/054781; WO 2008/040969). Thus, the stream of conclusion in this reaction comprises not only HFO-1234yf but also a not insignificant amount of HF.

The document WO 2011/059078 provides for the recovery of the HFO-1234yf from the mixture at the outlet of the hydrofluorination reaction by cooling said mixture in order to obtain an upper phase concentrated in HF and a lower phase concentrated in HFO-1234yf, followed by azeotropic distillation of the lower phase.

This document is concerned only with the purification of HFO-1234yf. In point of fact, it is found that the upper part concentrated in HF comprises a large amount of HFO-1234yf. Consequently, this upper part should also be subjected to a treatment if it is desired to recover HF in order to be reused in the hydrofluorination reaction without needlessly recycling the HFO-1234yf.

Furthermore, the document WO 2008/008519 describes, in example 5, the separation of an azeotropic composition of HFO-1234yf and HF by liquid/liquid extraction using an isomer of 1,2,3,3,3-pentafluoropropene at a temperature of −40° C. The compound used for the extraction is highly toxic.

The applicant company has now developed a process for the separation of a composition comprising 2,3,3,3-tetrafluoropropene and HF and for the recovery not only of the 2,3,3,3-tetrafluoropropene but also of the HF. This process does not exhibit the disadvantages of the prior art.

A first subject matter of the present invention is thus a process for the separation and recovery of 2,3,3,3-tetrafluoropropene and HF from a composition comprising 2,3,3,3-tetrafluoropropene and HF, characterized in that it comprises a stage of cooling (separating by settling) said composition in the presence of an added amount of at least one compound (C1) chosen from chlorocarbons, hydrochlorocarbons, hydrochlorofluorocarbons, optionally fluorinated alcohols, optionally fluorinated ethers, ketones, esters, polyols and hydrofluorinated ethers in order to give an upper phase concentrated in HF and a lower phase concentrated in HFO-1234yf and compound C1.

This stage of cooling in the presence of at least one compound C1 makes it possible to obtain an upper phase which is richer in HF with a very small amount of HFO-1234yf, which phase is capable of being used without any purification stage. The HF thus recovered can be directly recycled to a hydrofluorination reaction stage.

The lower organic phase comprises the compound C1, HFO-1234yf and possibly organic impurities. This organic phase can be subjected to a distillation stage in order to separate the compound C1 and HFO-1234yf. The compound C1 can be recycled to the cooling stage and/or to the reaction stage resulting in the formation of HFO-1234yf.

The HFO-1234yf/HF molar ratio in the composition to be separated is preferably between 0.5 and 2.5 and advantageously between 1.1 and 2.1.

The 2,3,3,3-tetrafluoropropene is preferably present in an azeotropic or quasi azeotropic amount with the HF in the composition to be separated.

Advantageously, the composition to be separated originates from a hydrofluorination or dehydrofluorination stage.

The compound C1 to be added to the composition for the cooling stage is a hydrohalocarbon compound which preferably comprises three carbon atoms. Mention may in particular be made of pentachloropropanes, in particular 1,1,1,2,3-pentachloropropane (HCC-240db), 1,1,2,2,3-pentachloropropane (HCC-240aa) and 1,1,1,2,2-pentachloropropane (HCC-240ab); tetrachlorofluoropropanes, in particular 1,1,2,3-tetrachloro-1-fluoropropane (HCFC-241db); trichlorodifluoropropanes; dichlorotrifluoropropanes, in particular 1,2-dichloro-3,3,3-trifluoropropane (HCFC-243db); chlorotetrafluoropropanes, in particular 2-chloro-1,1,1,2-tetrafluoropropane (HCFC-244bb); tetrachloropropenes, in particular 1,1,2,3-tetrachloropropene (HCO-1230xa) and 1,1,1,2-tetrachloropropene (HCO-1230xf); and chlorotrifluoropropenes, in particular 2-chloro-3,3,3-trifluoropropene (HCFO-1233xf).

Preferably, the compound to be added is the same as that which has reacted with HF to give the HFO-1234yf or the compound to be added is an intermediate in the hydrofluorination reaction resulting in the manufacture of the HFO-1234yf.

For example, when the HFO-1234yf is prepared by the hydrofluorination reaction on HCC-240db, the compound C1 is preferably HCC-240db or HCFO-1233xf.

Likewise, when the HFO-1234yf is prepared by the hydrofluorination reaction on HFO-1233xf, the compound C1 is preferably HFO-1233xf.

When the HFO-1234yf is prepared by the hydrofluorination reaction on HFO-1230xa, the compound C1 is preferably HFO-1230xa or HCFO-1233xf.

When the compound C1 is different from that which has reacted with HF to give HFO-1234yf, the preferred compound C1 is chosen from optionally fluorinated alcohols, optionally fluorinated ethers, ketones, esters, polyols and hydrofluorinated ethers.

Mention may in particular be made, as alcohol, of those having an alkyl group of 1 to 5 carbon atoms. The alcohol can also be fluorinated and the preferred fluorinated alcohol is chosen from the alkyl groups of 1 to 3 carbon atoms.

The ketones of formula RCOR' with R and R', which are identical or different, each representing an alkyl group of 1 to 5 carbon atoms may be suitable.

The esters of formula RCOOR' with R and R', which are identical or different, each representing an alkyl group of 1 to 5 carbon atoms may be suitable.

The ethers of formula ROR' with R and R', which are identical or different, each representing an alkyl group of 1 to 7 carbon atoms may be suitable.

The ethers may be partially or completely fluorinated. When the ethers are partially fluorinated, they are denoted by hydrofluorinated ether.

Preference is given, as hydrofluorinated ether, to that having a boiling point of between 0 and 250° C., advantageously between 20° C. and 200° C. and more advantageously between 20° C. and 150° C.

Mention may in particular be made of 2,2,2-trifluoroethyl difluoromethyl ether (HFE-245mf), 1,1,1,2,2-pentafluoroethyl methyl ether (HFE-245mc), 1,1,2,2-tetrafluoroethyl methyl ether (HFE-245pc), 1,1,2,3,3,3-hexafluoropropyl methyl ether (HFE-356mec) or 1,1,1,2,2,2-hexafluorodiethyl methyl ether (HFE-356mff).

The hydrofluorinated ether, such as heptafluoropropyl methyl ether (HFE-7000), nonafluorobutyl methyl ether/nonafluoroisobutyl methyl ether (HFE-7100), nonafluorobutyl ethyl ether (HFE-7200), decafluoro-3-methoxy-4-(trifluoromethyl)pentane (HFE-7300), 2-trifluoromethyl-3-ethoxydodecafluorohexane (HFE-7500) and the mixture of perfluoroisobutyl ethyl ether and perfluorobutyl ethyl ether (20-80% by weight) (HFE-8200), may be an advantage.

The polyols, such as ethylene glycols $RO(CH_2CH_2O)_nR'$ with n between 1 and 3 and R and R', which are identical or different, each representing a hydrogen atom or an alkyl group of 1 to 5 carbon atoms, may be suitable.

The amount of compound C1 to be added can represent from 5 to 95% by weight, with respect to the HFO-1234yf/HF mixture and preferably from 10 to 80% by weight, with respect to the HFO-1234yf/HF mixture.

The composition to be separated is preferably cooled to a temperature of between −20 and 40° C. and advantageously to a temperature of between −5 and 35° C. The cooling temperature depends both on the nature and on the amount of the compound C1 to be added. Thus, in the case of the addition a small amount of HCC-240db, the temperature of the cooling stage is preferably within the vicinity of 0° C., whereas it can reach ambient temperature (that is to say, 25° C.) in the presence of a greater amount of addition of the compound C1.

The pressure at which this cooling stage is carried out is between 0 and 40 bar, preferably between 0.3 and 25 bar and advantageously in the vicinity of the pressure of the reaction stage.

In addition to the HFO-1234yf and the HF, the composition to be separated can comprise organic impurities, such as HCFC-243db, HCFO-1233xf, 1,1,1,2,2-pentafluoropropane (HFC-245cb), 1,3,3,3-tetrafluoropropene (HFO-1234ze), 1-chloro-3,3,3-trifluoropropene (HFO-1233zd) and 3,3,3-trifluoropropene (HFO-1243zf).

These impurities are generally byproducts from the reaction stage.

Another subject matter of the present invention is a process for the purification of the HFO-1234yf. After the cooling stage, the HFO-1234yf is separated from the compound C1 of the organic phase, for example by distillation. The compound C1 can subsequently be recycled to the cooling stage and/or to the reaction stage when the compound C1 is a reactant or an intermediate of the reaction stage resulting in the formation of the HFO-1234yf.

The HFO-1234yf thus separated can subsequently be subjected to a purification stage in order to remove the impurities and possibly traces of HF.

Thus, when the HFO-1234yf is separated by distillation of the organic phase comprising C1, the gaseous effluent predominantly comprising HFO-1234yf resulting from the distillation column can be subjected to washing in washing columns comprising water and then comprising aqueous sodium hydroxide solution in order to remove any traces of acidity. The HFO-1234yf, free from its acidity, can subsequently be dried, compressed and liquefied, and finally purified using several distillation columns, making it possible to remove the light or heavy impurities originating from the preceding stages.

The advantage of the stage of cooling (separated by settling) according to the present invention is in part to maximize the recovery of HF and to minimize the amount of HF present in the organic phase, which is reflected by minimization in the effluents comprising HF. It also exhibits the advantage of minimizing the amount of HFO-1234yf recycled in the reaction stage in the phase enriched in HF. Furthermore, this separating by settling can be carried out at ambient temperature, which makes it possible to avoid cooling the mixture to very low temperatures and using a refrigerated unit, which exhibits a certain advantage in terms of energy.

In addition, a subject matter of the present invention is a process for the manufacture of HFO-1234yf comprising (i) at least one stage during which at least one saturated or unsaturated hydrocarbon compound having three carbon atoms and comprising at least one chlorine atom which reacts with HF in the presence of a fluorination catalyst, (ii) a stage of removal of HCl coproduced during stage (i), (iii) a stage of cooling according to the first subject matter of the invention and (iv) at least one stage of purification of HFO-1234yf of the organic phase obtained in (iii).

Preferably, the saturated or unsaturated hydrocarbon compound having three carbon atoms is chosen from HCC-240db, HCFO-1233xf and HCO-1230xa.

The stage of reaction with HF is preferably carried out in the gas phase.

According to a preferred embodiment of the present invention, the process for the manufacture of HFO-1234yf comprises (i) at least one reaction stage during which HCC-240db reacts in the gas phase with HF in the presence of a fluorination catalyst to give a stream comprising HFO-1234yf and its intermediates, for example HCFO-1233xf, HCl and excess HF; (ii) a stage of removal of HCl from the stream exiting from stage (i); (iii) a stage of cooling in the presence of the addition of the compound C1, preferably HCC-240db or HCFO-1233xf, to give an upper phase concentrated in HF and a lower phase concentrated in HFO-1234yf and comprising the compound C1; (iv) a stage of separation of the HFO-1234yf from the compound C1 and optionally recycling the compound C1 to the cooling stage (iii) or to stage (i); (v) a stage of purification of the HFO-1234yf; and (vi) optionally recycling of the upper phase rich in HF to stage (i).

In the presence of a large excess of HF used in the reaction stage, the process for the manufacture of HFO-1234yf according to the present invention can comprise, before the stage of removal of HCl, a stage of distillation in order to recover a portion of HF which can be recycled to the reaction stage.

FIG. 1 described below represents a preferred embodiment of the present invention.

HCC-240db (1) and HF (2), which are optionally preheated, are introduced into the reactor (101) containing a fluorination catalyst maintained at a temperature of between 300 and 450° C. The stream (102) at the outlet of the reactor, comprising HCl, HF, HFO-1234yf, HCFO-1233xf and HFC-245cb, is sent to a first column for distillation of the HF (103) to give, at the column top, a stream (104) comprising HCl, HFO-1234yf, HF and HFC-245cb and, at the column bottom, a stream (105) comprising HF, HCFO-1233xf and HFC-245cb.

The stream (104) is sent to a second distillation column (106) to give HCl at the top and a stream (107) at the bottom comprising HF, HFO-1234yf and HFC-245cb.

The stream (105) is recycled to the reactor (101).

The decanter (108), maintained at a temperature of between −5 and 35° C., is fed with the stream (107) and with the stream (110) comprising HCC-240db.

The lower phase (109) of the decanter, comprising HFO-1234yf and HCC-240db, is sent to a distillation column (112) to give, at the top, a stream essentially comprising HFO-1234yf (113) and, at the bottom, a stream (110) essentially comprising HCC-240db.

The stream (110) is recycled to the reactor (101) and/or to the decanter (108).

The upper phase (111) of the decanter, enriched in HF, is recycled to the reactor (101).

The stream (113) is sent to the washing columns (114) to give, at the top, a stream (115) freed from any acidity.

The stream (115) is finally sent to the purification stage (116) to give pure HFO-1234yf.

Experimental Part

A liquid composition containing 40 mol % of HF and 60 mol % of HFO-1234yf (i.e., 89.5% by weight) is cooled to atmospheric pressure at a temperature slightly greater than 15° C. There is no separation by settling.

At a temperature of less than 15° C., a lower organic phase is obtained which comprises more than 92% by weight of HFO-1234yf and an upper phase is obtained which comprises only 71% by weight of HF.

At −30° C., the upper phase contains only 78% by weight of HF and 22% by weight of HFO-1234yf, which remains very high. The lower organic phase contains 98.5% by weight of HFO-1234yf and 1.5% by weight of HF. The efficiency of the separation by settling is thus mediocre, even at low temperature.

EXAMPLES ACCORDING TO THE INVENTION

Example 1

A liquid composition containing 32.6% by weight of HFO-1234yf, 3.9% by weight of HF (HFO-1234yf/HF molar ratio=1.48) and 63.5% by weight of HCC-240db is cooled.

At a cooling temperature of 20° C., a lower organic phase is obtained which comprises 0.2% by weight of HF and an upper phase is obtained which comprises 88% by weight of HF and 10% by weight of HFO-1234yf.

At a cooling temperature of 0° C., a lower organic phase is obtained which comprises 0.1% by weight of HF and an upper phase is obtained which comprises 89% by weight of HF and 9% by weight of HFO-1234yf.

Example 2

A liquid composition containing 36.5% by weight of HFO-1234yf, 4.3% by weight of HF (HFO-1234yf/HF molar ratio=1.5) and 59.2% by weight of HCC-1230xa is cooled.

At a cooling temperature of 20° C., a lower organic phase is obtained which comprises 0.2% by weight of HF and an upper phase is obtained which comprises 86% by weight of HF and 11% by weight of HFO-1234yf.

At a cooling temperature of 0° C., a lower organic phase is obtained which comprises 0.15% by weight of HF and an upper phase is obtained which comprises 87% by weight of HF and 11% by weight of HFO-1234yf.

Example 3

A liquid composition containing 38.1% by weight of HFO-1234yf, 4.5% by weight of HF and 57.4% by weight of HCFC-243db is cooled.

At a cooling temperature of 20° C., a lower organic phase is obtained which comprises 0.1% by weight of HF and an upper phase is obtained which comprises 85% by weight of HF and 9% by weight of HFO-1234yf.

At a cooling temperature of −20° C., a lower organic phase is obtained which comprises less than 0.1% by weight of HF and an upper phase is obtained which comprises 88% by weight of HF and 9% by weight of HFO-1234yf.

Example 4

A liquid composition containing 43.6% by weight of HFO-1234yf, 5.2% by weight of HF and 51.2% by weight of HCFC-1233xf is cooled.

At a cooling temperature of 0° C., a lower organic phase is obtained which comprises 2% by weight of HF and an upper phase is obtained which comprises 77% by weight of HF and 11% by weight of HFO-1234yf.

Example 5

A liquid composition containing 40.4% by weight of HFO-1234yf, 4.8% by weight of HF and 54.8% by weight of HCFC-244bb is cooled.

At a cooling temperature of 20° C., a lower organic phase is obtained which comprises 1.5% by weight of HF and an upper phase is obtained which comprises 82% by weight of HF and 10% by weight of HFO-1234yf.

At a cooling temperature of 0° C., a lower organic phase is obtained which comprises 1% by weight of HF and an upper phase is obtained which comprises 84% by weight of HF and 9% by weight of HFO-1234yf.

The invention claimed is:
1. A process for the manufacture of 2,3,3,3-tetrafluoropropene, comprising (i) at least one reaction stage during which at least one saturated or unsaturated hydrocarbon compound having three carbon atoms and comprising at least one chlorine atom reacts in the gas phase with HF in the presence of a fluorination catalyst to give a stream comprising 2,3,3,3-tetrafluoropropene and intermediates of 2,3,3,3-tetrafluoropropene, HCl and excess HF; (ii) a stage of removal of HCl from the stream exiting from stage (i); (iii) a stage of cooling said stream exiting from stage (ii) in the presence of an added amount of at least one compound (C1) selected from the group consisting of chlorocarbons, hydrochlorocarbons, hydrochlorofluorocarbons, alcohols, fluorinated alcohols, ethers, fluorinated ethers, ketones, esters, polyols and hydrofluorinated ethers in order to separate an upper phase rich in HF from a lower organic phase rich in 2,3,3,3-tetrafluoropropene and compound C1, whereby said separating occurs by settling; (iv) a stage of separation of the 2,3,3,3-tetrafluoropropene from the lower phase; and (v) a stage of purification of the 2,3,3,3-tetrafluoropropene.

2. The process as claimed in claim 1, characterized in that it comprises a stage of distillation of HF before the stage of removal of HCl.

3. The process as claimed in claim 1, wherein in stage (iii), the 2,3,3,3-tetrafluoropropene/HF molar ratio is between 0.5 and 2.5.

4. The process as claimed in claim 1, wherein in stage (iii), the amount of compound C1 to be added represents from 5% to 95% by weight, with respect to the HFO-1234yf/HF mixture.

5. The process as claimed in claim 1, characterized in that the temperature in stage (iii) is between 20 and 40° C.

6. The process as claimed in claim 1, wherein the saturated or unsaturated hydrocarbon compound having three carbon atoms is chosen from 1,1,1,2,3-pentachloropropane, 1,1,2,3-tetrachloropropene and 2-chloro-3,3,3-trifluoropropene.

7. The process as claimed in claim 1, wherein the compound C1 is selected from the group consisting of 1,1,1,2,3-pentachloropropane, 1,1,2,3-tetrachloro-1-fluoropropane, 1,2-dichloro-3,3,3-trifluoropropane, 1,1,2,3-tetrachloropropene and 2-chloro-3,3,3-trifluoropropene.

8. The process as claimed in claim 1, wherein the compound C1 is selected from the group consisting of alcohols ROH, ketones RCOR', esters RCOOR', with R and R', which are identical or different, each representing an alkyl group of 1 to 5 carbon atoms, and ethers ROR', with R and R', which are identical or different, each representing an alkyl group of 1 to 7 carbon atoms.

9. The process as claimed in claim 1, wherein the compound C1 is the same as that which reacted with HF in the hydrofluorination stage.

10. The process as claimed in claim 1 wherein the part enriched in HF after the cooling stage is recycled to the hydrofluorination stage.

11. The process as claimed in claim 1, characterized in that the organic part, after separation of the 2,3,3,3-tetrafluoropropene is recycled to the cooling stage and/or to the reaction stage.

* * * * *